United States Patent [19]
Ouchi

[11] Patent Number: 5,976,073
[45] Date of Patent: Nov. 2, 1999

[54] HOOD OF ENDOSCOPE

[75] Inventor: Teruo Ouchi, Saitama-ken, Japan

[73] Assignee: Asahi Kogaku Kogyo Kabushiki Kaisha, Tokyo, Japan

[21] Appl. No.: 09/097,264

[22] Filed: Jun. 15, 1998

[30] Foreign Application Priority Data

Jun. 18, 1997 [JP] Japan ..................................... 9-160753

[51] Int. Cl.$^6$ .............................. A61B 1/22; A61B 17/24
[52] U.S. Cl. .......................... 600/129; 600/156; 606/113; 606/110
[58] Field of Search .................................... 600/104, 127, 600/129, 156; 606/110, 113, 114, 115

[56] References Cited

U.S. PATENT DOCUMENTS

| 5,417,697 | 5/1995 | Wilk et al. | 606/113 |
| 5,423,830 | 6/1995 | Schneebaum et al. | 606/115 |

FOREIGN PATENT DOCUMENTS 8131397  5/1996  Japan .

OTHER PUBLICATIONS

"Endoscopic Ligation of Esophageal Varices Using A Detachable Snare And Transparrent Cap With Rim", Tadashi Hachisu et al., Digestive Endoscopy, vol. 9, No. 3, 1997, pp. 183–188.

Primary Examiner—Jeffrey A. Smith
Attorney, Agent, or Firm—Greenblum & Bernstein P.L.C.

[57] ABSTRACT

An insertion tube has a suction opening and a view window provided to an end surface of a tip thereof. The hood includes an outer wall and a partition wall mounted to the tip of the insertion tube. The outer wall projects from the tip so as to surround the end surface of the tip. The partition wall is provided to divide a cavity surrounded by the outer wall into two cavities, in such a manner that the suction opening and the view window are separately located in the cavities.

23 Claims, 9 Drawing Sheets

HOOD OF ENDOSCOPE

BACKGROUND OF THE INVENTION

This invention relates to a hood which is mounted to the tip of an insertion tube of an endoscope.

Generally, the hood has a cylindrical wall surrounding the end surface of the insertion tube. A suction channel is provided in the insertion tube, which opens at an end surface of the insertion tube. The suction opening is located in a cavity surrounded by the cylindrical wall of the hood.

In order to remove the mucous membrane, an operator inserts the insertion tube into the human body so that the hood abuts the mucous membrane. Then, the operator performs a suction (via the suction opening). Since the suction opening is located in the cavity surrounded by the hood, the mucous membrane is sucked in the cavity so that the sucked mucous membrane forms a polyp. The operator cuts the polyp by means of a snare inserted through the suction channel.

During these process, the operator observes the mucous membrane through a view window provided to the tip of the insertion tube. Generally, the view window and the suction opening are provided on the same end surface of the insertion tube and similarly surrounded by the cylindrical hood.

However, when the suction is performed, the sucked mucous membrane reaches the vicinity of the view window, which may interfere with the view of the operator. With this, it is difficult for the operator to observe the mucous membrane well.

SUMMARY OF THE INVENTION

It is therefore an object of the present invention to provide a hood of an endoscope wherein an operator is able to observe a mucous membrane.

According to one aspect of the present invention, there is provided a hood which is mounted to an insertion tube of an endoscope. The insertion tube has a suction opening and a view window provided to an end surface of a tip thereof. The hood includes (1) an outer wall mounted to the tip of the insertion tube, the outer wall projecting from the tip so as to surround the end surface of the tip, and (2) a partition wall which divide a cavity surrounded by the outer wall into at least two cavities, in such a manner that the suction opening and the view window are separately located in the cavities.

With such an arrangement, when the suction is performed, the mucous membrane is sucked in one cavity where the suction opening exists, while the mucous membrane is not sucked in the other cavity where the view window is located. That is, the mucous membrane does not reach the vicinity of the view window. Thus, the view is not interfered, which enables an operator to observe the mucous membrane well.

In a particular arrangement, the outer wall has a cylindrical shape. The partition wall is a flat plate extending across a cavity surrounded by the outer wall.

Preferably, the hood is made of transparent material, so that the operator is able to observe a wide area through the transparent hood. Optionally, the hood is detachably mounted to the tip of the insertion tube. With this, the endoscope can be used for other purposes without the hood.

According to another aspect of the present invention, there is provided a hood including an outer wall mounted to the tip of the insertion tube. The outer wall projects from the tip and surrounds the suction opening so that the suction opening is located in a cavity surrounded by the outer wall. The outer wall is so formed that the view window is located out of the cavity.

With such an arrangement, since the view window is located out of the cavity, the mucous membrane does not reaches the vicinity of the view window when the suction is performed. Therefore, the view is not interfered, which enables an operator to observe the mucous membrane well. In a particular arrangement, the outer wall has a semi-cylindrical shape.

DESCRIPTION OF THE PREFERRED EMBODIMENT

The first embodiment of the present invention is described.

Figure 1:
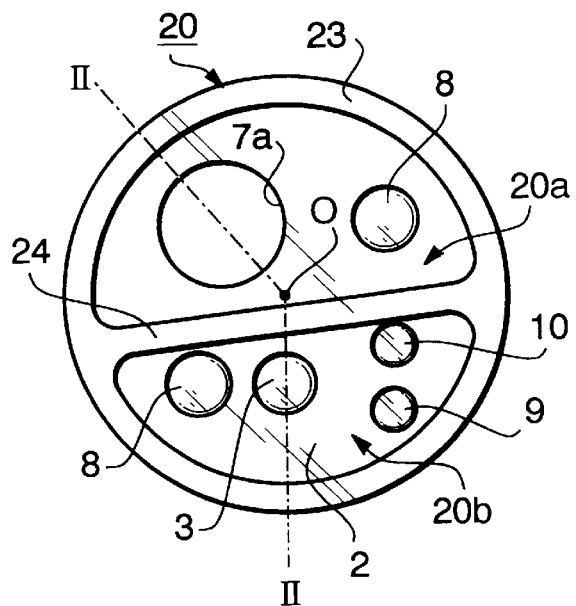
FIG. 1 is a front view of an insertion tube and a hood according to a first embodiment.
Figure 2:
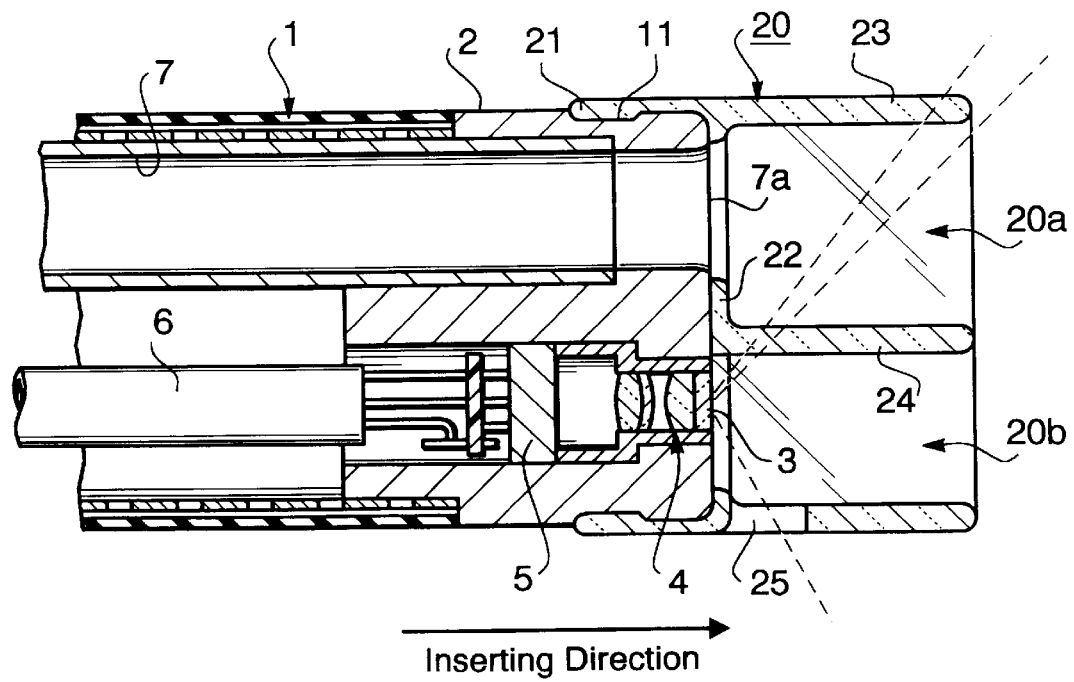
FIG. 2 is a sectional view of the insertion tube and the hood of FIG. 1.

FIG. 1 is a front view of an insertion tube of an endoscope and a hood according to the first embodiment. FIG. 2 is a sectional view of the insertion tube and the hood taken along line II—II of FIG. 1

As shown in FIG. 2, an endoscope includes an insertion tube 1. In this specification, a 'tip' is defined as a head end of the insertion tube 1 in the inserting direction. The insertion tube 1 has a view window 3 provided at a tip 2 of the insertion tube 1 and an object lens group 4 provided behind the view window 3. In order to capture an image viewed through the window 3, a CCD 5 is provided at an image plane of the object lens group 4. The image captured by the CCD 5 is sent (via cable 6) to a not-shown operating part of the endoscope.

The insertion tube 1 includes a suction channel 7 extending through the insertion tube 1. The suction channel 7 opens at an end surface of the insertion tube 1. The suction channel 7 is also used as an instrument tube through which instruments (such as a snare, an injector, or the like) are inserted. Alternatively, it is possible that a suction channel and an instrument channel are separately provided.

As shown in FIG. 1, the insertion tube 1 is further provided with two illumination windows 8, an air supply nozzle 9 and a water supply nozzle 10. With such an arrangement, the endoscope enables an operator to observe an illuminated object located in front of the tip of the insertion tube 1.

A hood 20 is detachably mounted to the tip of the insertion tube 1. The rear portion (the left portion in FIG. 2) of the hood 20 has a cylindrical shape. The hood 20 has projections 21 which inwardly project from an inner surface of the hood 20. The insertion tube 1 has a groove 11 which extends along the periphery of the tip of the insertion tube 1. The projections 21 of the hood 20 are fit into the groove 11, so that the hood 20 is mounted to the insertion tube 1. On detaching the hood 20 from the insertion tube 1, the hood 20 is pulled rightward in FIG. 2 so that the hood 20 is elastically deformed and that the projections 21 are moved out of the groove 11. The hood 20 is further provided with a contact wall 22 to which an end surface of the insertion tube 1 abuts when the hood 20 is mounted to the insertion tube 1. The contact wall 22 extends in a direction perpendicular to the axial direction of the hood 20. Further, the contact wall 22 is shaped so that the contact wall 22 does not interfere with the suction opening 7*a*, the view window 3, and the air and water supply nozzles 8 and 9. The hood 20 is made of a transparent plastic, so that the hood 20 does not interfere with the view through the view window 3.

The front portion (the right portion in FIG. 2) of the hood 20 has a cylindrical outer wall 23 and a partition wall 24 extending across a cavity surrounded by the outer wall 23. Due to the partition wall 24, a cylindrical cavity (surrounded by the outer wall 23) is divided into two cavities 20*a* and 20*b*: a first cavity 20*a* in which the suction opening 7*a* and one of the illumination windows 8 are located and a second cavity 20*b* in which the view window 3, the other of the illumination windows 8, the air and water supply nozzles 9 and 10 are located. As shown in FIG. 2, a leak hole 25 is formed on the outer wall 23, for leaking liquid in front of the view window 3 so that the liquid does not interfere with the view through the view window 3.

Figure 3:
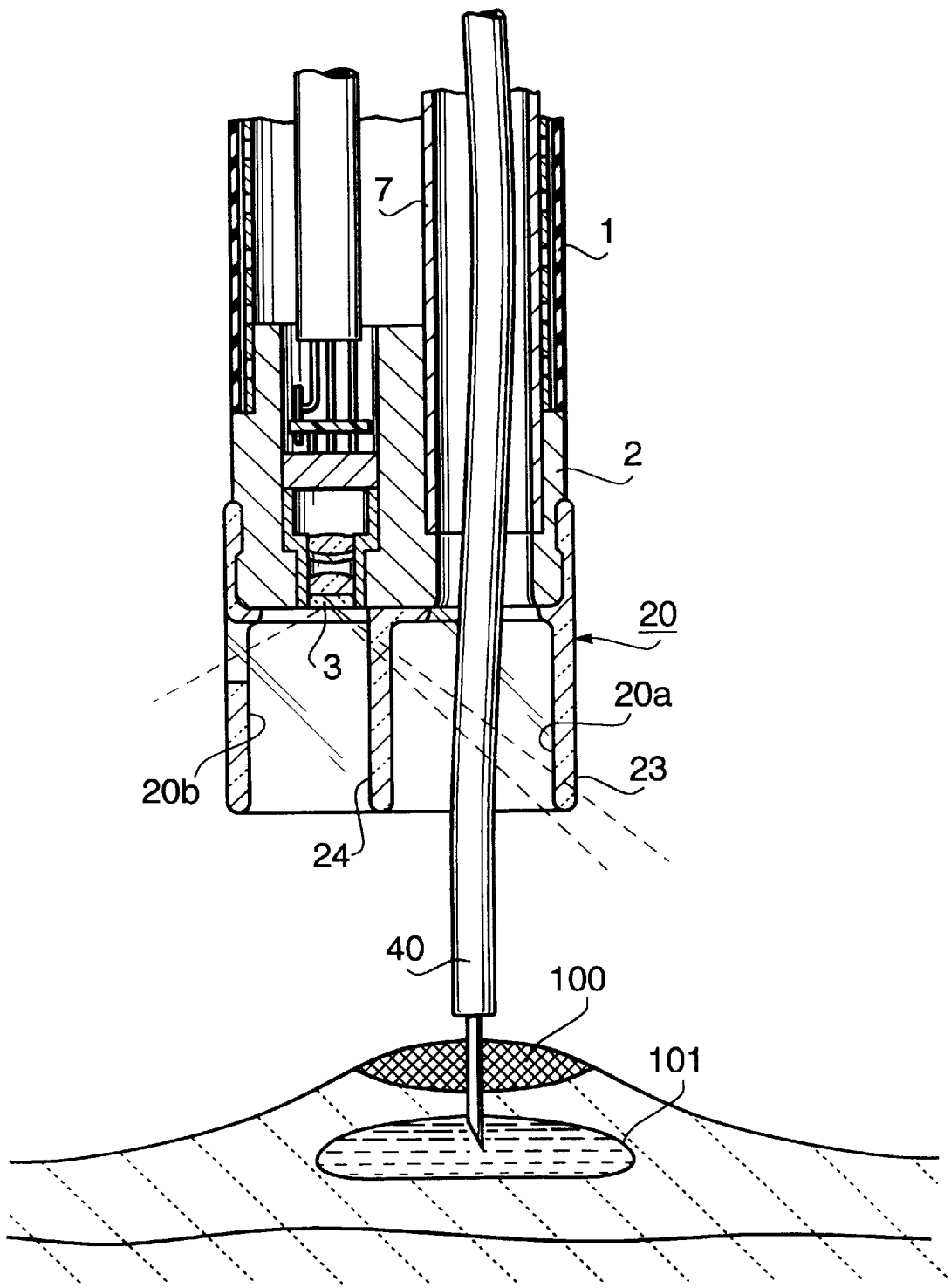
FIGS. 3, 4 and 5 are sectional views illustrating an operation of the endoscope of FIG. 1.
Figure 4:
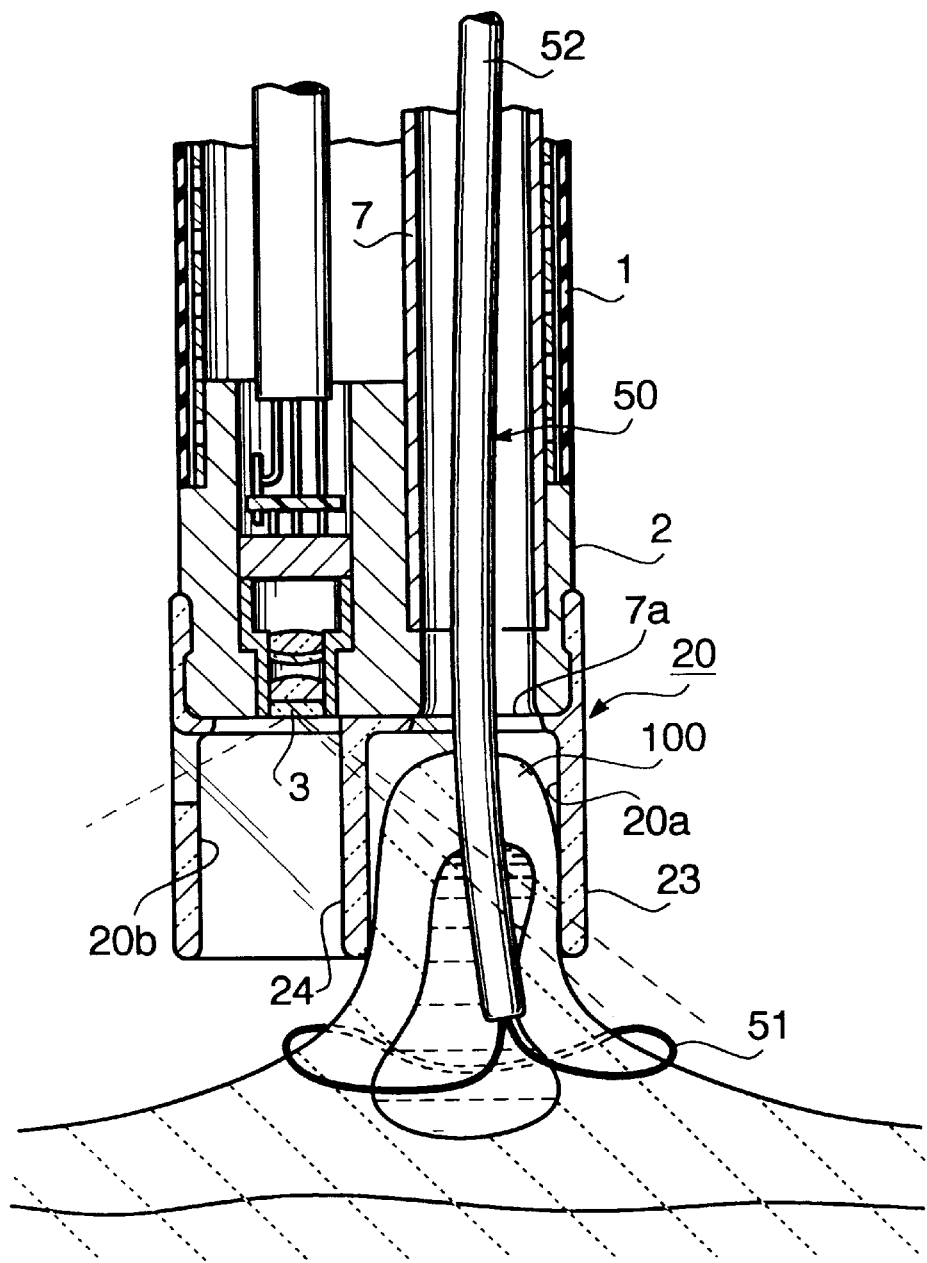
Figure 5:
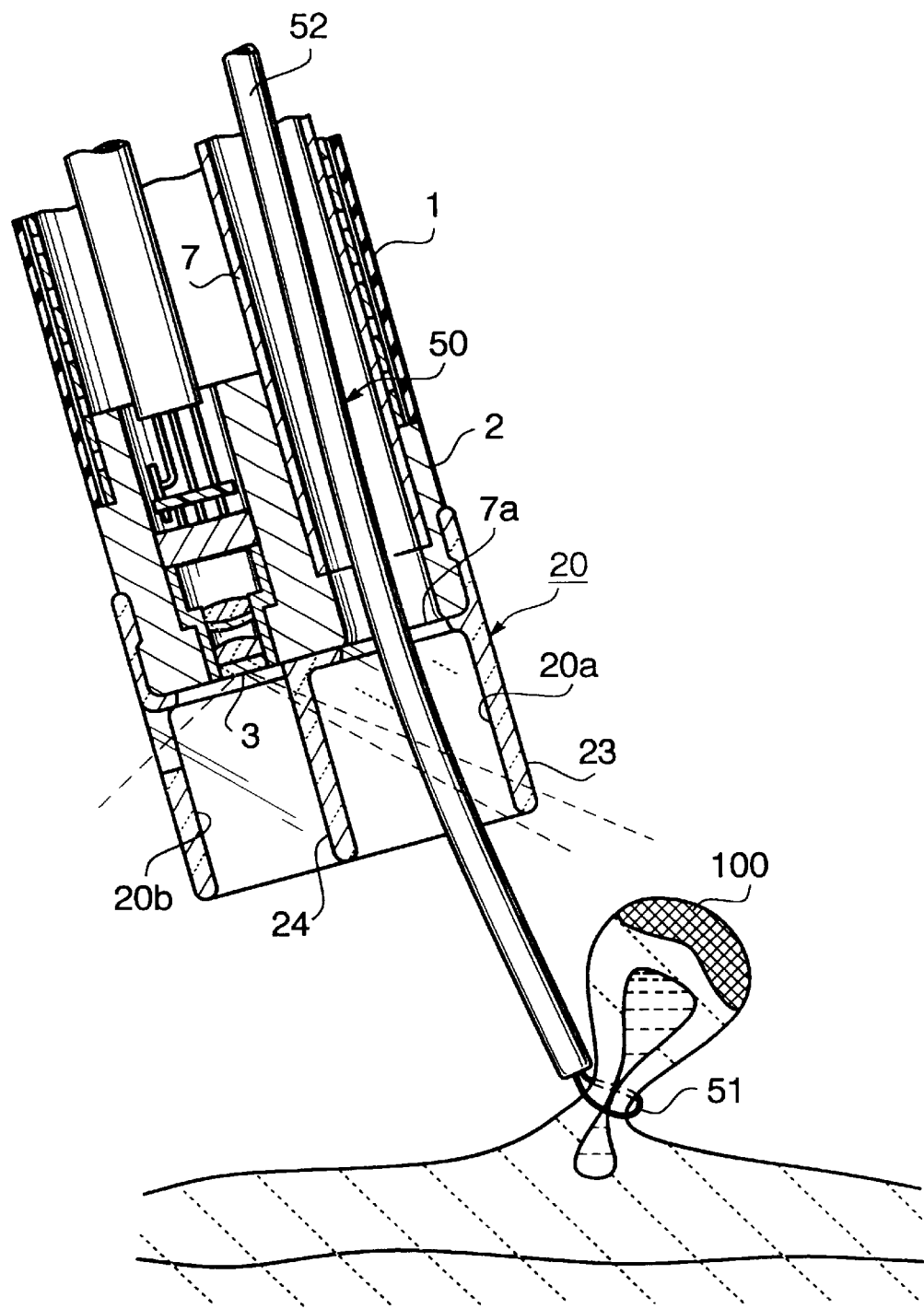

FIGS. 3 through 5 are sectional view illustrating an operation of the endoscope with the hood 20. As shown in FIG. 3, the insertion tube 1 (with the hood 20) is inserted into the human body. Then, an operator inserts an injector 40 through the suction channel 7, observing an affected mucous membrane 100 through view window 3. Further, the operator injects a physiological saline water 101 including hemostatic (by the injector 40) under the affected mucous membrane 100. With this, the affected mucous membrane 100 is bulged as shown in FIG. 3. Since the hood 20 is transparent, the operator is able to view a wide area around the affected mucous membrane 100 as shown by dashed lines in FIG. 3.

Then, as shown in FIG. 4, the operator inserts a high-frequency snare 50 through the suction channel 7. The high-frequency snare 50 includes a snare loop 51 and a sheath 52 provided around the snare loop 51. Further, the operator starts suction via the suction channel 7, so that the affected mucous membrane 100 is sucked in the first cavity 20*a* of the hood 20. With this, the affected mucous membrane 100 forms a polyp, which is surrounded by the snare loop 51. Since the affected mucous membrane 100 is not sucked in the second cavity 20*b*, the view window 3 is not interfered. Then, the operator closes the snare loop 51 (as shown in FIG. 5), stops the suction and allows current to flow in the snare loop 51 thereby to cut the polyp. Since the operator is able to operate this process observing the polyp and the snare loop 51 through the transparent hood 24, it is possible to accurately and safely cut the polyp.

As described above, according to the first embodiment, the suction opening 7*a* and the view window 3 are separately located in cavities 20*a* and 20*b*, respectively. Therefore, when the suction is performed, the mucous membrane is not sucked in the cavity 20*b*, while the mucous membrane is sucked in the cavity 20*a*. Thus, the view window 3 is not interfered by the sucked mucous membrane, which enables an operator to observe the mucous membrane well.

Figure 6:
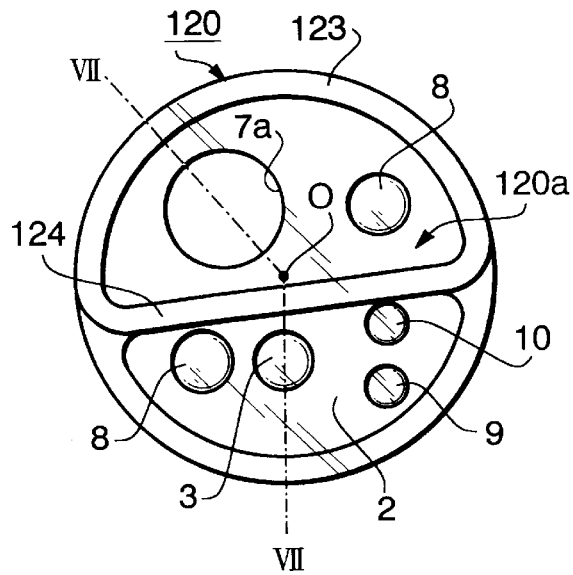
FIG. 6 is a front view of an insertion tube and a hood according to the second embodiment.
Figure 7:
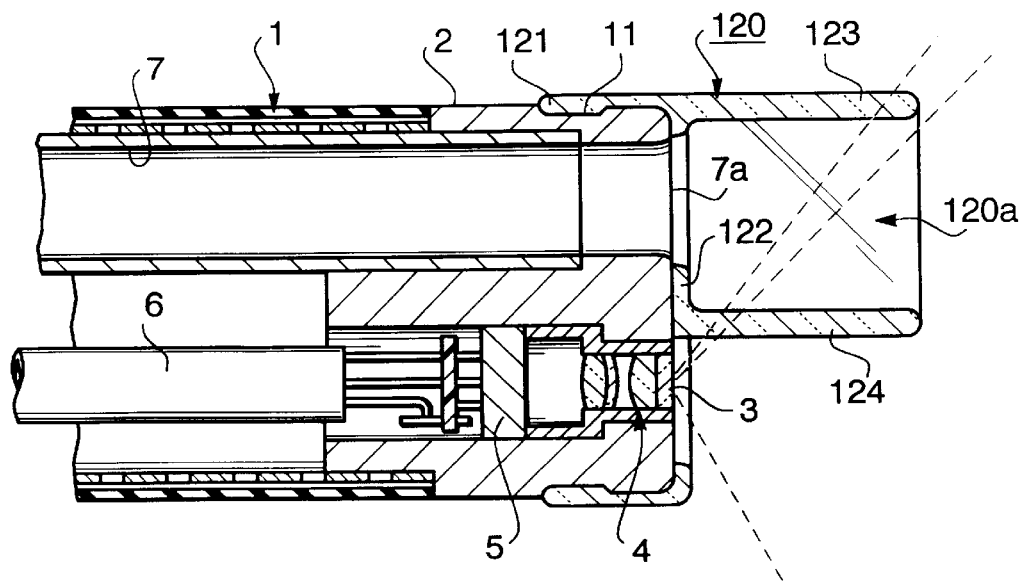
FIG. 7 is a sectional view of the insertion tube and the hood of FIG. 6.

The second embodiment of the present invention is described. FIG. 6 is a front view of an endoscope and a hood according to the second embodiment. FIG. 7 is a sectional view of the endoscope and the hood taken along line VII—VII of FIG. 6. In the second embodiment, the structure of the insertion tube 1 is same as that of the first embodiment.

As shown in FIGS. 6 and 7, a hood 120 of the second embodiment is semicircular shaped and includes an arced wall 123 and a plane wall 124. The arced wall 123 substantially extends along a half of a periphery of the tip of the insertion tube 1. The plane wall 124 extends between both ends of the arced wall 123. The suction opening 7*a* and one of the illumination windows 8 are located in a cavity 120*a* surrounded by the arced wall 123 and a plane wall 124. The view window 3, the other illumination window 8 and the air and water supply nozzles 9 and 10 are located outside of the cavity 120*a*. An arrangement for detachably mounting the hood 120 to the insertion tube 1 and including projections 121 is similar to the first embodiment.

Figure 8:
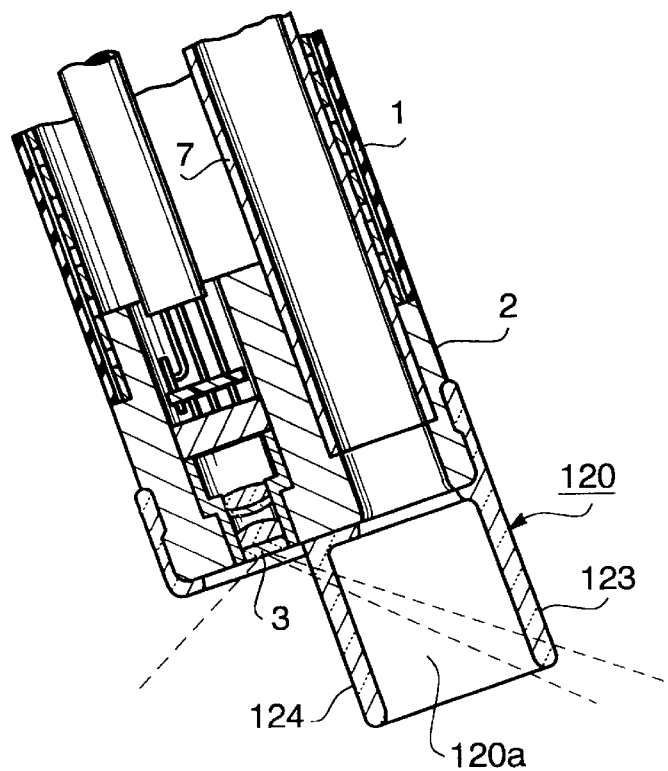
FIGS. 8, 9 and 10 are sectional views illustrating an operation of the endoscope of FIG. 6.
Figure 8:
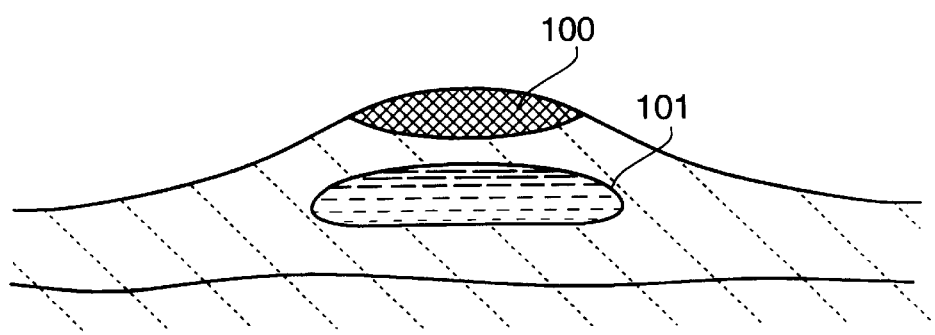
Figure 9:
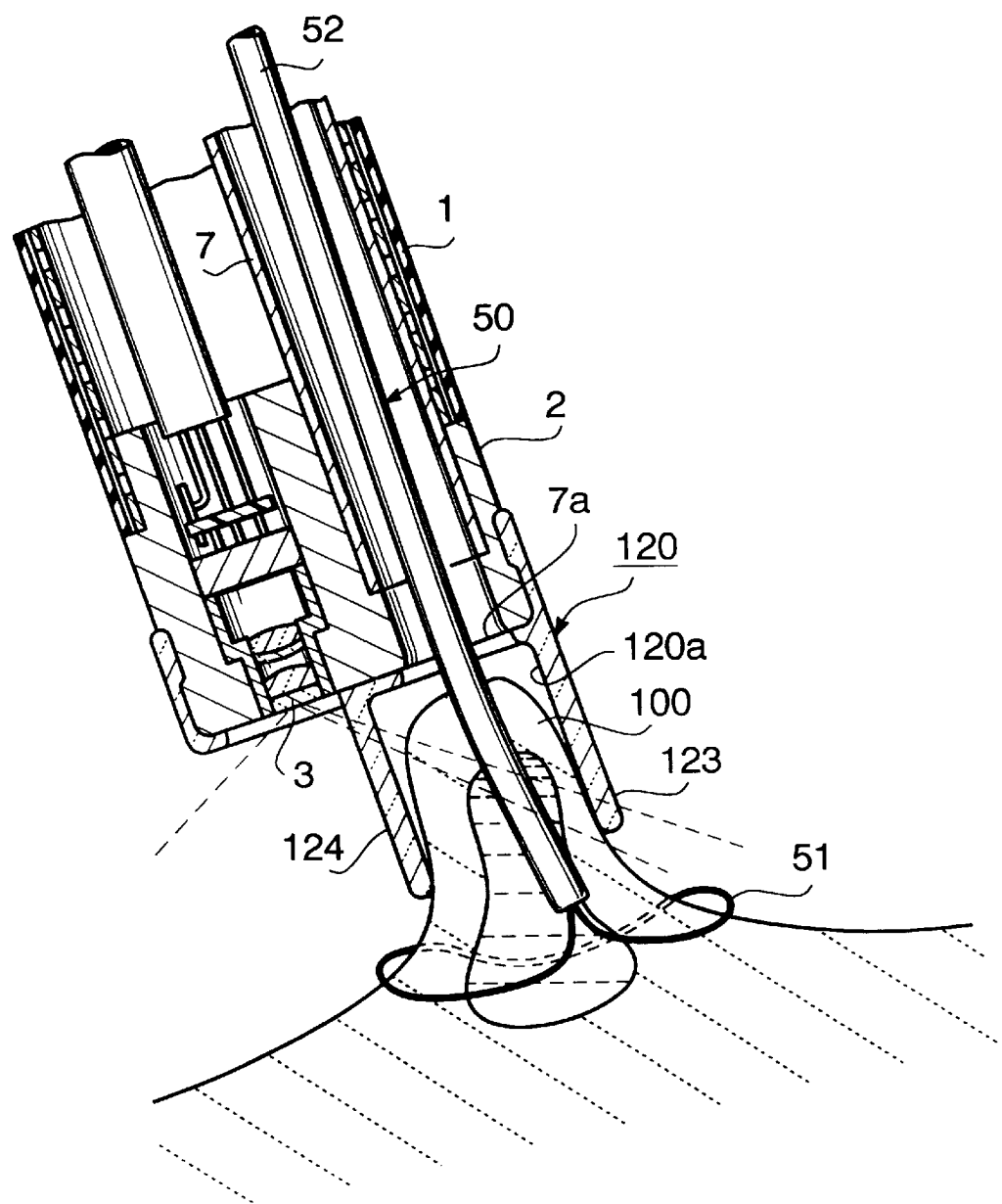
Figure 10:
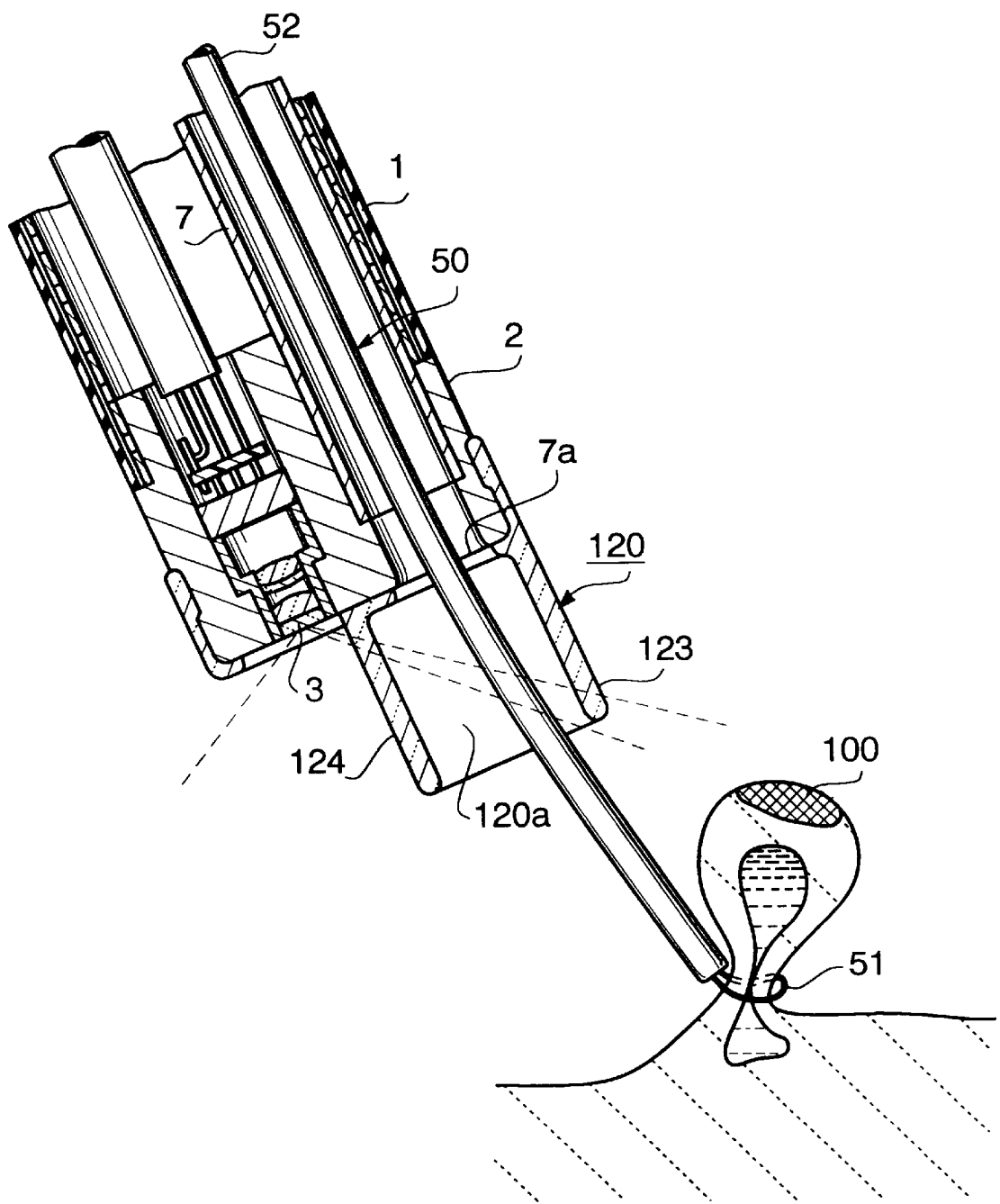

FIGS. 8 through 10 are sectional views illustrating an operation of the endoscope with the hood 120. As shown in FIG. 8, an operator inserts a not-shown injector through the suction channel 7, observing an affected mucous membrane 100 through the view window 3. The operator injects a physiological saline water including hemostatic (by the not-shown injector) under the affected mucous membrane 100. Since the hood 120 is transparent, and since the view window 3 is not fully surrounded by the hood 120, the operator is able to view a wide area around the affected mucous membrane 100. Then, as shown in FIG. 9, the operator inserts a high-frequency snare 50 through the suction channel 7. Further, the operator starts suction through the suction channel 7, so that the affected mucous membrane 100 is sucked in the cavity 120*a* of the hood 120. With this, the affected mucous membrane 100 forms a polyp, which is surrounded by a snare loop 51 of the snare 50. The operator closes the snare loop 51 (as shown in FIG. 10), stops the suction and allows current to flow in the snare loop 51 thereby to cut the polyp. Since the affected mucous membrane 100 is sucked in the cavity 120*a*, the view window 3 is not interfered. Similar to the first embodiment, it is possible to accurately and safely cut the polyp.

As described above, according to the second embodiment, the suction opening 7*a* is located in cavity 120*a*, while the view window 3 is located out of the cavity 120*a*. Therefore, the view (via the view window 3) is not interfered by the mucous membrane even when the suction is performed.

Figure 11:
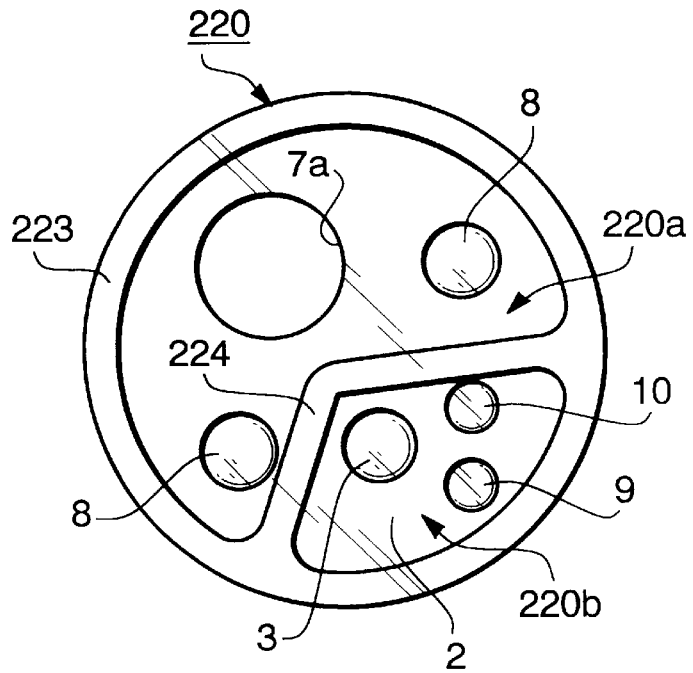
FIG. 11 is a front view of an insertion tube and a hood according to the third embodiment.

FIG. 11 is a front view of the insertion tube and the hood of the third embodiment. In the third embodiment, the structure of the insertion tube 1 is the same as that of the first embodiment. The hood 220 of the third embodiment includes a cylindrical outer wall 223 and a partition wall 224. The partition wall 224 extends so as to divide a cavity surrounded by the cylindrical outer wall 223 into large and small cavities 220*a* and 220*b*: a large cavity 220*a* in which the suction opening 7*a* and the illumination windows 8 are located and a small cavity 220*b* in which the view window 3 and the air and water supply nozzle 9 and 10 are located. Other structure is the same as the first embodiment. The hood 220 is made of transparent material.

With such an arrangement, since the suction opening 7*a* is located in the large cavity 220*a*, the area of the mucous membrane which can be sucked by suction is relatively large.

Figure 12:
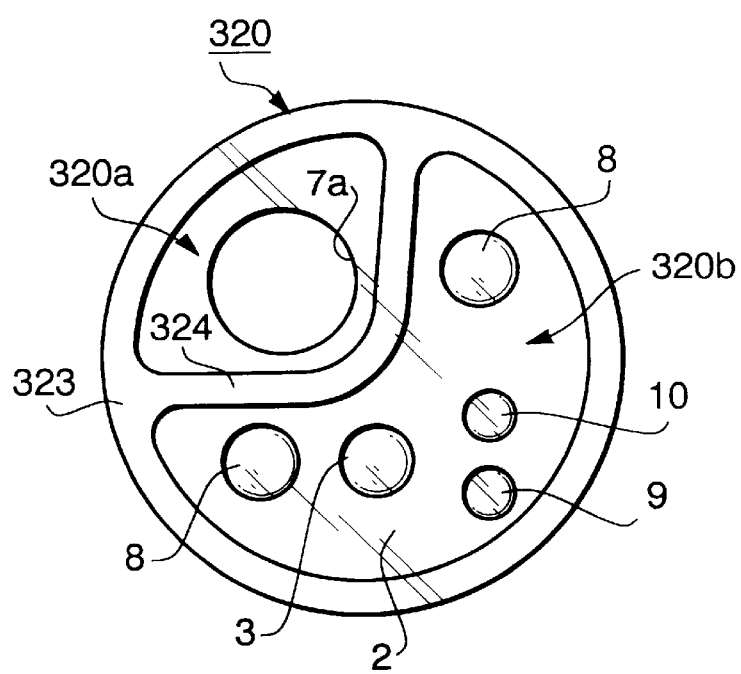
FIG. 12 is a front view of an insertion tube and a hood according to the fourth embodiment.

FIG. 12 is a front view of the insertion tube and the hood of the fourth embodiment. In the fourth embodiment, the structure of the insertion tube 1 is the same as that of the first embodiment. The hood 320 of the fourth embodiment includes a cylindrical outer wall 323 and a partition wall 324. The partition wall 324 extends so as to divide a cavity surrounded by the cylindrical outer wall 323 into small and large cavities 320a and 320b: a small cavity 320a in which the suction opening 7a is located and a large cavity 320b in which the view window 3, the illumination windows 8 and the air and water supply nozzle 9 and 10 are located. Other structure is the same as the first embodiment. The hood 320 is made of transparent material.

With such an arrangement, the partition wall 324 of the hood 320 is relatively far from the view window 3, compared with the first to third embodiments. Therefore, the area seen through the transparent hood 320 (by the view window 3) is relatively small, while the area seen directly by the view window 3 is relatively large. It enhances a quality of image seen through the view window 3.

Although the structure and operation of a hood of an endoscope is described herein with respect to the preferred embodiments, many modifications and changes can be made without departing from the spirit and scope of the invention.

The present disclosure relates to subject matters contained in Japanese Patent Application No. HEI 09-160753, filed on Jun. 18, 1997, which is expressly incorporated herein by reference in their entirety.

What is claimed is:

1. A hood mounted to an insertion tube of an endoscope, said insertion tube having a suction opening and a view window provided to an end surface of a tip thereof, said hood comprising:
   an outer wall mounted to said tip of said insertion tube, said outer wall projecting from said tip so as to surround said end surface of said tip; and
   a partition wall which divides a cavity surrounded by said outer wall into at least two cavities, in such a manner that said suction opening and said view window are separately located in said cavities.

2. The hood according to claim 1, wherein said outer wall has a cylindrical shape.

3. The hood according to claim 2, wherein said partition wall is a flat plate extending across a cavity surrounded by said outer wall.

4. The hood according to claim 1, wherein said hood is made of transparent material.

5. The hood according to claim 1, wherein said hood is detachably mounted to said tip of said insertion tube.

6. The hood according to claim 1, wherein said cavity is divided into two cavities by said partition wall.

7. The hood according to claim 6, wherein one of said two cavities is larger than the other of said cavities.

8. The hood according to claim 7, wherein said suction opening is located in a larger cavity of said cavities.

9. The hood according to claim 7, wherein said view window is located in a larger cavity of said cavities.

10. An endoscope unit:
    an insertion tube which is inserted into a human body;
    a suction channel provided in said insertion tube so that said suction channel opens at an end surface of a tip of said insertion tube,
    a view window provided at said end surface of said tip of said insertion tube,
    an outer wall mounted to said tip of said insertion tube, said outer wall projecting from said tip so as to surround said end surface of said tip; and
    a partition wall which divides a cavity surrounded by said outer wall into at least two cavities, in such a manner that said suction opening and said view window are separately located in said cavities.

11. The endoscope unit according to claim 10, wherein said tip of said insertion tube has a tubular shape, while said outer wall has a cylindrical shape.

12. The endoscope unit according to claim 10, wherein said hood is made of transparent material.

13. The endoscope unit according to claim 10, wherein said suction channel is also used as an instrument channel through which an instrument is inserted into said human body.

14. The endoscope unit according to claim 10, wherein said insertion tube has at least one illumination opening, and
    wherein at least one illumination opening is located in a same cavity as said view window.

15. The endoscope unit according to claim 10, wherein said insertion tube and said hood have engaging portions which engage with each other, so that said hood is detachably mounted to said insertion tube.

16. A hood mounted to an insertion tube of an endoscope,
    said insertion tube having a suction opening and a view window provided to an end surface of a tip thereof, said hood comprising:
    an outer wall mounted to said tip of said insertion tube, said outer wall projecting from said tip and surrounding said suction opening so that said suction opening is located in a cavity surrounded by said outer wall; said outer wall is so formed that said view window is located out of said cavity.

17. The hood according to claim 16, wherein said outer wall has a semi-cylindrical shape.

18. The hood according to claim 16, wherein said outer wall is made of transparent material.

19. The hood according to claim 18, wherein said hood is detachably mounted to said tip of said insertion tube.

20. An endoscope unit:
    an insertion tube which is inserted into a human body;
    a suction channel provided in said insertion tube so that said suction channel opens at an end surface of a tip of said insertion tube,
    a view window provided at said end surface of said tip of said insertion tube; and
    an outer wall mounted to said tip of said insertion tube, said outer wall projecting from said tip and surrounding said suction opening so that said suction opening is located in a cavity surrounded by said outer wall,
    wherein said outer wall is so formed that said view window is located out of said cavity.

21. The endoscope unit according to claim 20, wherein said suction channel is also used as an instrument channel through which an instrument is inserted into said human body.

22. The endoscope unit according to claim 20, wherein said insertion tube has at least one illumination opening, and
    wherein at least one illumination opening is located out of said cavity.

23. The endoscope unit according to claim 20, wherein said insertion tube and said hood have engaging portions which engage with each other, so that said hood is detachably mounted to said insertion tube.

* * * * *